United States Patent [19]

Cunkle et al.

[11] Patent Number: 5,844,025
[45] Date of Patent: Dec. 1, 1998

[54] 1,2-BIS-ADDUCTS OF STABLE NITROXIDES WITH SUBSTITUTED ETHYLENES AND STABILIZED COMPOSITIONS

[75] Inventors: Glen Thomas Cunkle, Stamford, Conn.; Thomas F. Thompson, Yonkers, N.Y.; Volker H. von Ahn, Mahopac, N.Y.; Roland A. E. Winter, Armonk, N.Y.

[73] Assignee: Ciba Specialty Chemicals Corporation, Tarrytown, N.Y.

[21] Appl. No.: 755,882

[22] Filed: Dec. 2, 1996

[51] Int. Cl.$^6$ .......................................................... C08K 5/34
[52] U.S. Cl. ................................. 524/99; 524/87; 524/98; 524/102; 524/103; 524/104; 524/105; 526/204; 546/191
[58] Field of Search .................................. 524/99, 87, 98, 524/102, 103, 104, 105; 526/204; 546/191

[56] References Cited

U.S. PATENT DOCUMENTS 5,322,960  6/1994  Sakamoto et al. ....................... 560/205

OTHER PUBLICATIONS

Journal of Fluorine Chemistry 69(1994) 163–169 A.E. Tipping, et al.

J. Chemical Society C, 901(1966)—R.E. Banks, et al.

J. Chemical Society C, 2777(1971)—R.E. Banks, et al.

Polymer Bulletin 6, 589(1982) G. Moad, et al.

*Primary Examiner*—Frederick Krass
*Attorney, Agent, or Firm*—Luther A. R. Hall

[57] ABSTRACT

1,2-Bis-adducts of stable hindered nitroxide compounds with substituted ethylenes are prepared by reacting two equivalents of nitroxyl compound with an ethylenically unsaturated compound such as styrene or an acrylate ester. These adducts are very effective inhibitors to prevent the premature polymerization of ethylenically unsaturated monomers when such monomers are distilled, processed or stored.

4 Claims, No Drawings

1,2-BIS-ADDUCTS OF STABLE NITROXIDES WITH SUBSTITUTED ETHYLENES AND STABILIZED COMPOSITIONS

The instant invention pertains to novel 1,2-adducts of stable hindered nitroxyl compounds with substituted ethylenes such as found in ethylenically unsaturated monomers. The adducts are very effective inhibitors for preventing the premature polymerization of vinyl monomers.

BACKGROUND OF THE INVENTION

Many of the industrially important ethylenically unsaturated monomers are highly susceptible to unwanted radical polymerization initiated either thermally or by adventitious impurities. Some examples of these monomers are styrene, acrylic and methacrylic acid, acrylate and methacrylate esters and acrylonitrile. Premature polymerization may occur during manufacture, purification or storage of the monomer. Many of these monomers are purified by distillation. It is in this operation where premature polymerization is most likely to occur and to be the most troublesome. Methods to prevent or reduce the amount of such polymerization are thus highly desirable since the prevention or mitigation of such premature polymerization increases the yield of purified monomer and also insures against costly and potentially dangerous runaway polymerization in the plant.

Stable hindered organic nitroxyl compounds included in this invention are those nitroxides which are fully substituted at the alpha carbon atoms. See L. B. Volodarsky et al., Synthetic Chemistry of Stable Nitroxides, CRC Press, Boca Raton, FL, 1994. Bis-trifluoromethylnitroxide is a stable nitroxide and its 1,2-bis-adducts with ethylenes are known. See A. E. Tipping et al., J. Fluor. Chem., 69, 163 (1994); R. E. Banks et al., J. Chem. Soc. C, 901 (1966); and R. E. Banks et al., J. Chem. Soc., C, 2777 (1971).

1-Phenyl-1,2-bis(2,2,6,6-tetramethylpiperidin-1-yloxy)-ethane is a known bis-adduct G. Moad et al., Polymer Bull. 6, 589 (1982) reported this material as prepared by the reaction of 1-oxyl-2,2,6,6-tetramethylpiperidine with styrene. No chemical Abstract Number was ever assigned to this compound nor was any utility ever ascribed to such compounds.

OBJECTS OF THE INVENTION

One object of this invention is to provide novel bis-adduct compounds formed by the reaction of stable hindered organic nitroxyl compounds with an ethylenically unsaturated monomer.

Another object of this invention is to demonstrate the ability of these bis-adducts to prevent or mitigate the premature polymerization of ethylenically unsaturated monomers during distillation and purification.

Still another object of this invention is to provide compounds which exhibit effective stabilization efficacy to organic substrates subject to thermal or light induced radiation.

DETAILED DISCLOSURE

The instant invention pertains to novel 1,2-bis-adducts of formula I or II

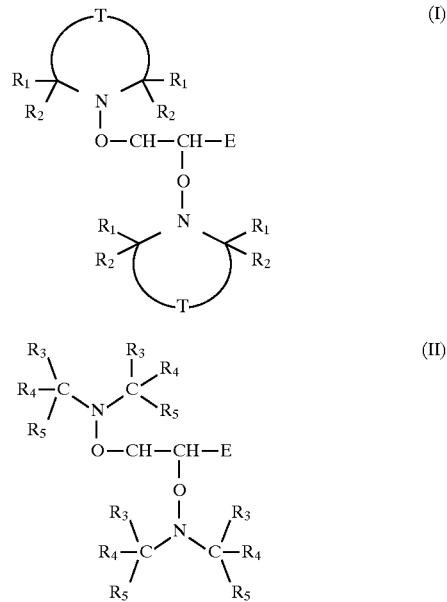

where $R_1$ and $R_2$ are independently alkyl of 1 to 4 carbon atoms, or $R_1$ and $R_2$ together are pentamethylene, preferably $R_1$ and $R_2$ are each methyl;

E is aryl of 6 to 10 carbon atoms, or said aryl substituted by alkyl of 1 to 4 carbon atoms or by halogen, or E is —COOH or —COOR$_6$ where R$_6$ is alkyl of 1 to 18 carbon atoms or hydroxyalkyl of 2 to 8 carbon atoms, or E is —CN, preferably E is —COOH, —CN or —COOR$_6$ where R$_6$ is alkyl of 1 to 4 carbon atoms, most preferably butyl;

$R_3$, $R_4$ and $R_5$ are independently alkyl of 1 to 4 carbon atoms, preferably methyl; and T is a group needed to complete a 5-, 6- or 7-membered ring or an 1,1,3,3-tetramethylisoindoline moiety, said T group can also be substituted by hydroxyl, by oxo, by acetamido, by —OR$_8$ where R$_8$ is alkyl of 1 to 18 carbon atoms, or by —O—CO—R$_9$ where R$_9$ is alkyl of 1 to 17 carbon atoms or phenyl, preferably R$_9$ is alkyl of 1 to 11 carbon atoms or phenyl.

Formula I represents adducts of cyclic 5-, 6- and 7-membered ring stable nitroxides. Formula II represents adducts of acyclic stable nitroxides.

Another aspect of the instant invention is the use of the bis-adducts of formulas I and II as effective inhibitors against the premature polymerization of ethylenically unsaturated monomers. The monomers are any having at least one carbon-carbon double bond capable of undergoing free radical induced polymerization. Such monomers are well-known in commerce and comprise a wide variety of structural types. Typical examples of such monomers are the vinyl aromatic hydrocarbons such as styrene, α-methylstyrene and divinylbenzene; dienes such as butadiene and isoprene; halogenated monomers such as vinyl chloride, chloroprene, vinylidene chloride, vinylidene fluoride and vinyl fluoride; unsaturated acids such as acrylic acid, methacrylic acid and crotonic acid, unsaturated esters such as the acrylates and methacrylates exemplified by butyl acrylate, methyl methacrylate, ethyl acrylate and methyl acrylate; unsaturated nitriles such as acrylonitrile and methacrylonitrile; unsaturated ethers such as methyl vinyl ether; and miscellaneous vinyl monomers such as the vinyl pyridines, diethyl vinylphosphonate and sodium styrenesulfonate.

Preferably the monomer is styrene, acrylic acid, methacrylic acid, butyl acrylate, ethyl acrylate or acrylonitrile; most preferably styrene.

The monomer composition stabilized against premature polymerization comprises (a) an ethylenically unsaturated monomer, and (b) an effective stabilizing amount of a compound of formula I or II as described above.

The effective stabilizing amount of component (b) is 1 to 10000 ppm by weight based on the weight of monomer of component (a). Preferably, the amount of component (b) is 10 to 1000 ppm by weight based on the monomer of component (a).

The activated polymerization inhibitor mixtures can be introduced into the monomer to be protected by any conventional method It may be added just upstream of the point of desired application by any suitable means. In addition, this mixture may be injected separately into the distillation train along with the incoming feed of monomer or through separate entry points providing efficient distribution of the activated inhibitor mixture. Since the inhibitor is gradually depleted during operation, it is generally necessary to maintain the appropriate amount of the activated inhibitor mixture in the distillation system by adding additional inhibitor during the course of the distillation process. Such addition may be carried out either on a continuous basis or by intermittently charging fresh inhibitor into the distillation system if the concentration of the inhibitor is to be maintained above the minimum required level.

The instant invention also pertains to a stabilized composition which comprises (a) an organic material subject to the deleterious effects of heat, oxygen or actinic radiation, and (b) an effective stabilizing amount of a compound of formula I or II as described above.

The organic material is preferably a polymer, especially a polyolefin, such as polypropylene or polyethylene, or a polymer, copolymer or polymer blend which contains in at least one polymer or polymer component significant ethylenic unsaturation. Examples of the latter are polymers selected from the group consisting of ABS, HIPS, emulsion SBR, PP/EPDM, PP/NBR, PP/NR, ABS/PC, ABS/nylon, ABS/PVC, ABS/polyester, ABS/SMA, ABS/polysulfone, ASA/PC, acetal/elastomer, polyester/elastomer, nylon/elastomer, PPO/NR, EPDM/NBR and EPDM/olefin.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(α-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, /isoprene/styrene, /ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from $\alpha,\beta$-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxy-benzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBIP/ABS.
28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention are employed from about 1 to about 20% by weight of the stabilized composition, although this will vary with the particular substrate and application. An advantageous range is from I to 5%; preferably 1.5 to 2.5%.

The resulting stabilized compositions of the instant invention may optionally also contain from about 0.01 to about 5%, preferably from about 0.025 to about 2%, and especially from about 0.1 to about 1% by weight of various conventional additives, such as the materials listed below, or mixtures thereof.

Other compositions of special interest include those which additionally contain a UV absorber selected from the group consisting of the benzophenones, benzotriazoles, cyanoacrylic acid derivatives, hydroxyaryl-s-triazines, organic nickel compounds and oxanilides.

Preferred UV absorbers are selected from the group consisting of 2-[2-hydroxy-3,5-di-($\alpha,\alpha$-dimethylbenzyl) phenyl]-2H-benzotriazole, 2-[2-hydroxy-3-($\alpha,\alpha$-dimethylbenzyl)-5octylphenyl]-2H-benzotriazole, 2-(2-hydroxy-3,5-di-tert-amylphenyl)-2H-benzotriazole, 2-[2-hydroxy-3-tert-butyl-5-($\omega$-hydroxy-octa(ethyleneoxy) carbonyl)ethylphenyl]-2H-benzotriazole, 2-[2-hydroxy-3-tert-butyl-5-(2-octyloxycarbonylethyl)phenyl]-2H-benzotriazole, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'ethyloxanilide, 2,6-bis(2,4-dimethylphenyl)-4-(2-hydroxy-4-octyloxyphenyl-s-triazine, 2,6-bis(2,4-dimethylphenyl)-4-(2,4-dihydroxyphenyl)-s-triazine, 2,4-bis(2,4-dihydroxyphenyl)-6-(4-chlorophenyl)-s-triazine, 2,6-bis(2,4-dimethylphenyl)-4-[2-hydroxy-4-(2-hydroxy-3-dodecyloxypropanoxy)-phenyl]-s-triazine and 2,2'-dihydroxy-4,4'-dimethoxybenzophenone.

Additional compositions of interest include those which additionally contain an effective stabilizing amount of a phenolic antioxidant; those which additionally contain a hindered amine derivative; or which additionally contain a phosphite or phosphonite stabilizer.

Compositions of special interest also include those wherein the organic material is an enamel of high solids content used for an industrial finish; is used as a coil coating; is used as a penetrating wood finish or is used as a film-forming wood finish.

When the instant compounds also contain a reactive functional group, said compounds can be chemically bonded by either condensation or free radical addition reaction to the polymer substrate. This provides for a non-migrating, non-sublimable UV absorber stabilizer. Such reactive functional groups include hydroxy, amino, amido, carboxyl and ethylenically unsaturated moieties.

The various organic materials useful in the instant invention are described in detail later in this application as well as are the various coadditives whose concomitant use with the instant compounds is often found to be highly beneficial.

The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.
1. Antioxidants
1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-($\alpha$-methylcyclohexyl)-4,6-dimethylphenol 2,6-di-octadecyl-4-methylphenol
2,4,6-tri-cyclohexylphenol
2,6-di-tert-butyl-4-methoxymethylphenol
    1.2. Alkylated hydroquinones, for example,
2,6-di-tert-butyl-4-methoxyphenol
2,5-di-tert-butyl-hydroquinone
2,5-di-tert-amyl-hydroquinone
2,6 diphenyl-4-octadecyloxyphenol
    1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
    1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.
    1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) iso-cyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
    1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
    1.7. Esters of β-(3,5-di-tert-butyl-4-hydroxyphenyl)-propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid diamide
    1.8. Esters of β-(5-tert-butyl-4-hydroxy-3-methylphenyl)-propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid diamide
    1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine
    2. UV absorbers and light stabilizers
    2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-α-cumyl-5'-tert-octyl, 3'-tert-butyl-5'-(2-(omega-hydroxy-octa-(ethyleneoxy)carbonyl-ethyl)-, 3'-odecyl-5'-methyl-, and 3'-tert-butyl-5'-(2-octyloxycarbonyl)ethyl-, and dodecylated-5'-methyl derivatives.
    2.2. 2-Hydroxy-benzophenones, for example, the 4-hydroxy-, 4-methoxy-, 4-octoxy, 4-decyloxy-, 4dodecyloxy-, 4-benzyloxy, 4,2',4'-trihydroxy- and 2'-hydroxy-4,4'-di-methoxy derivatives.
    2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.
    2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, a-carbomethoxy-p-methoxy-cinnamic acid methyl ester, N-(β-carbomethoxy-β-cyanovinyl)-2-methyl-indoline.
    2.5. Nickel compounds, for example, nickel complexes of 2,2'-thio-bis-[4-(1,1,3,3-tetra-methylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.
    2.6. Sterically hindered amines, for example bis-(2,2,6,6-tetramethylpiperidyl) sebacate, bis-(1,2,2,6,6- pentamethylpiperidyl) sebacate, n-butyl-3,5-di-tertbutyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilo-triacetate, tetrakis-(2,2,6,6-tetramethyl-4-piperidyl) 1,2,3,4-butanetetracarboxylate, 1,1' (1,2-ethanediyl)-bis-(3,3,5,5-tetramethylpiperazinone).

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis [2-hydroxy4(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxyl-amine, N,N-dioctylhydroxylamine, N,N-dilaurylhydroxylamine, N,N-ditetradecyl-hydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy) ethyl]iso-cyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxy-anilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-i-tert-butyl-4-hydroxybenzylmercaptoacetate, bis(3,5-di-tert-butyl4hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis-(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6- tert-octylamino-s-triazine and 4,4'-hexamethylenebis (amino-2,2,6,6-tetramethyl-piperidine), polycondensation product of 1-(2-hydroxyethyl)-2,2,6,6-tetra-methyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-1,2,2,6,6-pentamethyl-piperidin4-yl)-amino-s-triazin-2-yl]-1,10-diamino-4,7-di azadecane, mixed [2,2,6,6-tetramethylpiperidin-4-yl/β,β,β',β'-tetra-methyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/β,β,β',β'-tetramethyl-3,9-(2,4,8,10-tetraoxa-spiro[5.5]undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetra-methylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6tert-octyl-amino-s-triazine and 4,4'-hexamethylenebis(amino-2,2,6,6-tetramethylpiperidine), N,N',N'',N'''-tetrakis[(4,6-bis(butyl-(1,2,2,6,6-pentamethyl-piperidin-4-yl)amino)-s-triazine-2-yl]-1,10-diamino-4,7-diazadecane. di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The following examples are meant to illustrate the instant invention and are not to be construed to limit the scope of the instant invention in any manner whatsoever.

EXAMPLE 1

1,2-Bis-adduct of 1-Oxyl-2,2,6,6-tetramethyl-4-benzoyloxypiperidine and Styrene

A deoxygenated solution of 10 g of 1-oxyl-2,2,6,6-tetramethyl-4-benzoyloxypiperidine in 120 mL of styrene is heated at 100° C. for 24 hours. The unreacted styrene is then removed under reduced pressure. The title compound is isolated from the residue by chromatography and purified by crystallization from hexane/ethyl acetate to give 5.3 g of adduct product, melting at 175°–176° C.

EXAMPLE 2

1,2-Bis-adduct of 1-Oxyl-2,2,6,6-tetramethyl-4-benzoyloxypiperidine and 4-Chlorostyrene When following the procedure of Example 1, an equivalent amount of 4-chlorostyrene is substituted for styrene, the title compound is obtained after purification by chromatography as a white solid melting at 76°–78° C.

EXAMPLE 3

1,2-Bis-adduct of 1-Oxyl-2,2,6,6-tetramethyl-4-hydroxypiperidine and Styrene

When following the procedure of Example 1, an equivalent amount of 1-oxyl-2,2,6,6-tetramethyl-4-hydroxypiperidine is substituted for 1-oxyl-2,2,6,6tetramethyl-4-benzoyloxypiperidine, the tide compound is obtained after purification by chromatography as a white solid melting at 104°–108° C.

EXAMPLE 4

1,2-Bis-adduct of 1-Oxyl-2,2,6,6-tetramethylpiperidine and Styrene

When following the procedure of Example 1, an equivalent amount of 1-oxyl-2,2,6,6-tetramethylpiperidine is substituted for 1-oxyl-2,2,6,6tetramethyl-4benzoyloxypiperidine, the title compound is obtained after purification by chromatography as a colorless oil.

EXAMPLE 5

1,2-Bis-adduct of 1-Oxyl-2,2,6,6-tetramethyl-4-oxopiperidine and Styrene

When following the procedure of Example 1, an equivalent amount of 1-oxyl-2,2,6,6-tetramethyl-4-oxopiperidine is substituted for 1-oxyl-2,2,6,6-tetramethyl-4-benzoyloxypiperidine, the title compound is obtained after purification by chromatography as a colorless waxy solid.

EXAMPLE 6

1,2-Bis-adduct of 2-Oxyl-1,1,3,3-tetramethylisoindoline and Styrene

When following the procedure of Example 1, an equivalent amount of 2-oxyl-1,1,3,3-tetramethylisoindoline is substituted for 1-oxyl-2,2,6,6-tetramethyl-4-benzoyloxypiperidine, the title compound is obtained after purification by chromatography as a white solid melting at 138°–139° C.

EXAMPLE 7

1,2-Bis-adduct of 1-Oxyl-2,2,6,6-tetramethyl-4-benzoyloxypiperidine and Butyl Acrylate A deoxygenated solution of 30 g of 1-oxyl-2,2,6,6-tetramethyl-4-benzoyloxypiperidine in 50 mL of butyl acrylate is heated at 130° C. for 22 hours. The unreacted butyl acrylate is then removed under reduced pressure. The title compound is isolated from the residue by chromatography to give 9.0 g of adduct product as a colorless oil.

EXAMPLE 8

1,2-Bis-adduct of 1-Oxyl-2,2,6,6-tetramethyl-4-hydroxypiperidine and Butyl Acrylate When following the procedure of Example 7, an equivalent amount of 1-oxyl-2,2,6,6-tetramethyl-4-hydroxypiperidine is substituted for 1-oxyl-2,2,6,6-tetramethyl-4-benzoyloxypiperidine, the title compound is obtained after purification by chromatography as a white solid melting at 115°–117° C.

EXAMPLES 9–15

Commercial grade styrene is freed of the tert-butylcatechol storage stabilizer by washing with 1N aqueous sodium hydroxide followed by distillation under reduced pressure.

A 300-mL three-necked flask equipped with a thermometer, condenser, rubber septum and magnetic stirrer bar is charged with 100 g of styrene (purified as described above) without any inhibitor (Example 9) or charged in separate experiments with 200 mg of various test compounds of this invention in Examples 10–15. An oxygen-free atmosphere is established by five consecutive evacuations and backfilling with nitrogen, followed by sparging the styrene solution with pure nitrogen for 15 minutes. The vessel is immersed into a mechanically stirred and thermostatically controlled oilbath at 120° C. Small aliquots are removed periodically and analyzed for polymer content. The amount of polystyrene formed is then determined by refractive index measurements, calibrated with authenic polystyrene in styrene solutions of known concentrations. The results are shown in the table below.

| Compound of | | Percent Polymer Formed after Heating | | |
|---|---|---|---|---|
| Example | Example | 30 minutes | 60 minutes | 90 minutes |
| 9 | none | 3.7 | 8.4 | — |
| 10 | 1 | 0.0 | 0.5 | 2.8 |
| 11 | 2 | 0.0 | 0.8 | 3.8 |
| 12 | 3 | 0.0 | 0.2 | 1.6 |
| 13 | 4 | 0.0 | 0.0 | 1.0 |
| 14 | 5 | 0.1 | 0.1 | 1.9 |
| 15 | 6 | 0.0 | 0.2 | 1.3 |

It is clear from these data that each of the instant adduct compounds of Examples 10–15 provide far superior inhibition efficacy to prevent or mitigate the premature polymerization of the styrene monomer compared to the uninhibited styrene sample of Example 9.

EXAMPLE 16

1,2-Bis-adduct of 1-Oxyl-2,2,6,6-tetramethyl-4-acetamidopiperidine and Styrene When following the procedure of Example 1, an equivalent amount of 1-oxyl-2,2,6,6-tetramethyl-4-acetamidopiperidine is substituted for 1-oxyl-2,2,6,6-tetramethyl-4-benzoyloxypiperidine, the tide compound is obtained after purification by chromatography.

EXAMPLE 17

Light Stabilization of ABS/Polycarbonate Blends

A 50/50 blend of ABS (containing a hindered amine stabilizer compound of formula I) and polycarbonate is prepared by compounding the mixed resin pellets in a mini Brabender extruder. Injection molded 125 mil (3.2 mm) Izod bars are then prepared for evaluation of light stability, under standard interior automotive Xenon Arc WeatherOmeter exposure and spray Xenon Arc WeatherOmeter exposure tests.

The ABS/Polycarbonate blend containing the instant stabilizer compound of formula I shows enhanced light stabilization compared to control polymer having no hindered amine compound present.

EXAMPLE 18

Stabilization of Polypropylene Fiber

When a polypropylene fiber contains a stabilizer compound of formula I, it exhibits superior light and thermal stability compared to an unstabilized polypropylene fiber.

What is claimed is:

1. A stabilized composition which comprises the following components (a) and (b):
   (a) polypropylene, polyethylene or a polymer, copolymer or polymer blend which is or comprises at least one polymer which contains ethylenic unsaturation, and
   (b) an effective stabilizing amount of a compound of formula I or II

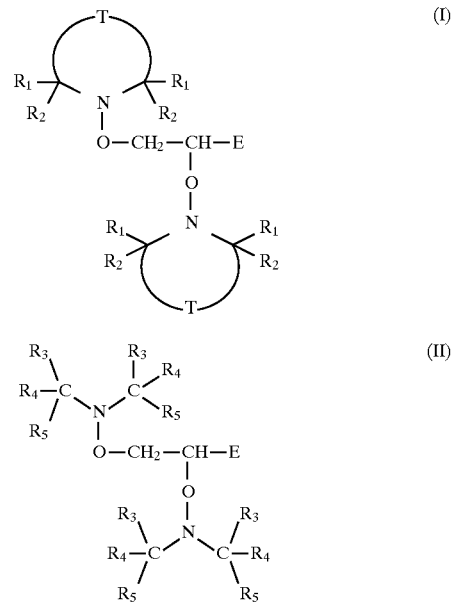

where $R_1$ and $R_2$ are independently alkyl of 1 to 4 carbon atoms, or $R_1$ and $R_2$ together are pentamethylene, E is aryl of 6 to 10 carbon atoms, or said aryl substituted by alkyl of 1 to 4 carbon atoms or by halogen, or E is —COOH or —COOR$_6$ where $R_6$ is alkyl of 1 to 18 carbon atoms or hydroxyalkyl of 2 to 8 carbon atoms, or E is —CN, $R_3$, $R_4$ and $R_5$ are independently alkyl of 1 to 4 carbon atoms, and T is a group needed to complete a 5-, 6- or 7-membered ring or an 1,1,3,3-tetramethylisoindoline moiety, where said T group is unsubstituted or substituted by hydroxyl, by oxo, by —OR$_8$ where $R_8$ is alkyl of 1 to 18 carbon atoms, or by —O—CO—R$_9$ where $R_9$ is alkyl of 1 to 17 carbon atoms or phenyl.

2. A composition according to claim 1 wherein component (c) is polypropylene or polyethylene.

3. A composition according to claim 1 wherein component (a) is a polymer, copolymer or polymer blend which is or comprises at least one polymer which contains ethylenic unsaturation.

4. A composition according to claim 3 wherein component (a) is selected from the group consisting of ABS, HIPS, emulsion SBR, PP/EPDM, PP/NBR, PP/NR, ABS/PC, ABS/nylon, ABS/PVC, ABS/polyester, ABS/SMA, ABS/polysulfone, ASA/PC, acetavelastomer, polyester/elastomer, nylon/elastomer, PPO/NR, EPDM/NBR and EPDM/olefin.

* * * * *